(12) United States Patent
Fukui et al.

(10) Patent No.: US 8,356,924 B2
(45) Date of Patent: Jan. 22, 2013

(54) LIGHT SOURCE APPARATUS

(75) Inventors: Yoshie Fukui, Tokyo (JP); Takeshi Ito, Tokyo (JP)

(73) Assignee: Olympus Corporation, Tokyo (JP)

( * ) Notice: Subject to any disclaimer, the term of this patent is extended or adjusted under 35 U.S.C. 154(b) by 544 days.

(21) Appl. No.: 12/569,031

(22) Filed: Sep. 29, 2009

(65) Prior Publication Data

US 2010/0080016 A1    Apr. 1, 2010

(30) Foreign Application Priority Data

Sep. 29, 2008   (JP) ................................. 2008-250968

(51) Int. Cl.
*F21V 8/00* (2006.01)
(52) U.S. Cl. ........... 362/574; 362/84; 362/554; 362/556
(58) Field of Classification Search .................. 362/574, 362/84, 554, 556, 572, 575, 581; 600/160, 600/176, 177, 178, 182
See application file for complete search history.

(56) References Cited

U.S. PATENT DOCUMENTS

| | | | | |
|---|---|---|---|---|
| 3,832,028 A | * | 8/1974 | Kapron | ............................ 385/43 |
| 4,721,359 A | * | 1/1988 | Nishioka et al. | .............. 385/117 |
| 6,217,205 B1 | * | 4/2001 | Ward | ............................ 362/580 |
| 7,422,356 B2 | * | 9/2008 | Hama et al. | .................... 362/574 |
| 7,744,358 B2 | * | 6/2010 | Kasono | ............................. 425/3 |
| 2008/0051632 A1 | | 2/2008 | Ito et al. | |

FOREIGN PATENT DOCUMENTS

JP          2006-296499         11/2006

* cited by examiner

*Primary Examiner* — Sharon Payne
(74) *Attorney, Agent, or Firm* — Scully Scott Murphy & Presser, PC

(57) ABSTRACT

A light source apparatus includes a light source from which, excitation light is emitted, an optical fiber which is optically connected to the light source, and which guides the excitation light, and a wavelength converting member which is optically connected to an emitting end portion of the optical fiber, and which receives the excitation light emitted from the emitting end portion, and makes emerge light of a wavelength area different from a wavelength area of the excitation light. The light source apparatus has a diverging unit which is arranged in an optical path of the excitation light, between the emitting end portion of the optical fiber and the wavelength converting member, and a holding member for holding the emitting end portion of the optical fiber, the diverging unit, and the wavelength converting member.

14 Claims, 14 Drawing Sheets

LIGHT SOURCE APPARATUS

CROSS-REFERENCE TO RELATED APPLICATION

The present application is based upon and claims the benefit of priority from the prior Japanese Patent Application No. 2008-250968 filed on Sep. 29, 2008; the entire contents of which are incorporated herein by reference.

BACKGROUND OF THE INVENTION

1. Field of the Invention

The present invention relates to a light source apparatus in which a solid light emitting element such as an LED, an SLD, and an LD is used.

2. Description of the Related Art

As a light source apparatus for an endoscope, a light source apparatus such as a xenon lamp, a halogen lamp, or a metal halide has hitherto been used. However, the light source apparatus such as the xenon lamp has a large size and high cost, and a light guiding efficiency up to an irradiated light emitting portion at a front end of the endoscope is low.

With regard to such problem, a conventional light source apparatus for endoscope has been disclosed in Japanese Patent Application Laid-open. Publication No. 2006-296499. FIG. 14 is a diagram showing a cross-sectional structure of main components of a conventional light source apparatus for endoscope 500. The conventional light source apparatus for endoscope 500 has a holding member 502 which is mounted on an endoscope inserting portion which is to be inserted into a body to be checked, a phosphor 509 which is fixed to the holding member 502, a laser light source not shown in the diagram, which irradiates laser light to fluorescent bodies 509a, 509b, and 509c, a light guide 524 which guides excitation light emitted from the laser source, and a convex lens 534 which spreads the excitation light emitted from the light guide 524. This is a light source apparatus in which, the excitation light emitted from the laser source is irradiated to the phosphor 509, and the phosphor 509 irradiates light of a wavelength different from a wavelength of the excitation light, to an area to be observed of the body to be checked. In this conventional light source apparatus for the endoscope, an arrangement is made such that the excitation light emitted from an emitting end portion Po of the light guide 524 is spread by the convex lens 534, and the excitation light is irradiated to a wide area of the phosphor 509. Therefore, it is possible to emit fluorescent light from the wide area of the phosphor 509.

SUMMARY OF THE INVENTION

A light source apparatus according to the present invention includes a light source which emits excitation light, an optical fiber which is optically connected to the light source, and which guides the excitation light, and a wavelength converting member which is optically connected to an emitting end portion of the optical fiber, and which receives the excitation light emitted from the emitting end portion, and makes emerge light of a wavelength area different from a wavelength area of the excitation light, and the light source apparatus has a diverging unit (diverging means) which is arranged in an optical path of the excitation light, between the emitting end portion of the optical fiber and the wavelength converting member.

Moreover, according to a preferable aspect of the present invention, it is desirable that the diverging unit has a function of widening a beam spot such that, a size of a beam spot formed on the wavelength converting member by the excitation light emitted form the optical fiber is substantially same as or smaller than a size of an effective wavelength conversion area of the wavelength converting member.

Furthermore, according to a preferable aspect of the present invention, it is desirable that the diverging unit includes at least an optical member having a negative refracting power which guides light.

According to a preferable aspect of the present invention, it is desirable that the diverging unit is a plurality of light diverging optical elements formed on a plate member.

Moreover, according to a preferable aspect of the present invention, it is desirable that the plurality of light diverging optical elements formed on the plate member is a concavo-convex surface formed on a surface of the plate member.

Furthermore, according to a preferable aspect of the present invention, it is desirable that a distance between a valley of a concave portion and a peak of a convex portion of the concavo-convex surface is not more than 100 microns.

According to a preferable aspect of the present invention, it is desirable that the light diverging optical element has a concavo-convex surface formed by an imprint method, on a surface of glass or resin.

Moreover, according to a preferable aspect of the present invention, it is desirable that the concavo-convex surface is disposed at random such that a distance between the convex portion and an adjacent convex portion is not more than 100 microns.

Furthermore, according to a preferable aspect of the present invention, it is desirable that the light diverging element is a plurality of concave lenses formed on a surface of the plate member.

According to a preferable aspect of the present invention, it is desirable that a size of the light diverging unit is substantially same or larger as compared to the beam spot formed on the light diverging unit by the excitation light.

Moreover, according to a preferable aspect of the present invention, it is desirable that a size of the wavelength converting member is substantially same or larger with respect to a beam spot formed on the wavelength converting member by the excitation light via the light diverging unit.

Furthermore, according to a preferable aspect of the present invention, it is desirable that the light source apparatus further includes a holding member which holds the emitting end portion of the optical fiber, the light diverging unit, and the wavelength converting unit, and an area between the emitting end portion of the optical fiber and the wavelength converting member, on an inner surface of the holding member is a circular conical structure having a taper angle with respect to a principal axis of the excitation light, and having a side toward the wavelength converting member wider than a side toward the emitting end portion of the optical fiber.

According to a preferable aspect of the present invention, it is desirable that the circular conical structure on the inner surface of the holding member has a first taper angle θ defined as an angle between the principal axis of the excitation light and the inner surface of the holding member, between the emitting end portion of the optical fiber and the light diverging unit, and a second taper angle ψ defined as angle between the principal axis of the excitation light and the inner surface of the holding member, between the light diverging unit and the wavelength converting member, mutually different.

Moreover, according to a preferable aspect of the present invention, it is desirable that the second taper angle ψ is greater with respect to the first taper angle θ.

Furthermore, according to a preferable aspect of the present invention, it is desirable that when an angle of incidence φ of the excitation light emitted from the emitting end portion of the optical fiber is calculated as $\phi = \sin^{-1}$ NA by using the number of aperture NA of the optical fiber, the first taper angle θ and the angle of incidence φ of the excitation light are related by a relation $\theta \geq \phi$.

According to a preferable aspect of the present invention, it is desirable that the inner surface of the holding member between the emitting end portion of the optical fiber and the wavelength converting member is a reflecting surface.

Moreover, according to a preferable aspect of the present invention, it is desirable that the light diverging unit is one concave lens, and the light source apparatus further includes an optical unit (optical means) which includes at least one convex lens between the light diverging unit and the wavelength converting member, which irradiates the excitation light spread by the light diverging unit, to the wavelength converting member, upon changing the excitation light to parallel light.

DETAILED DESCRIPTION OF THE INVENTION

Exemplary embodiments of a light source apparatus according to the present invention will be described below in detail by referring to the accompanying diagrams. However, the present invention is not restricted by the embodiments described below.

First Embodiment

Figure 1:
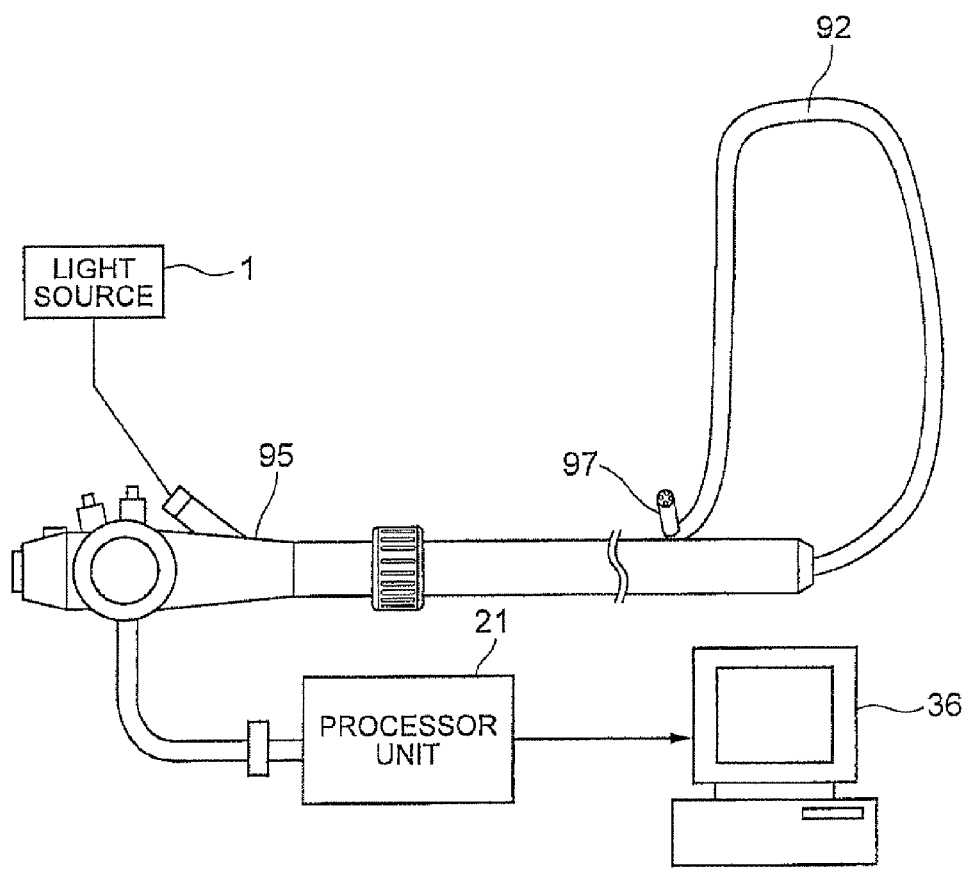
FIG. 1 is a diagram showing an overall structure of a semiconductor light source apparatus which can be used in an endoscope.

A semiconductor light source apparatus which can be used in an endoscope, according to a first embodiment of the present invention will be described below while referring to FIG. 1 and FIG. 2. FIG. 1 is a diagram showing an overall structure of the semiconductor light source apparatus which can be used in an endoscope, and FIG. 2 is a diagram showing a structure of main components of the semiconductor light source apparatus.

As shown in FIG. 1, the semiconductor light source apparatus of the first embodiment includes an endoscope insert portion 92, a endoscope front-end unit portion 97 which is connected to one end portion of the endoscope insert portion 92, an operating portion 95 which is connected to the other end portion of the endoscope insert portion 92, a light source 1 which supplies excitation light to a optical fiber which is disposed inside the operating portion 95 and the endoscope insert portion 92, a processor unit 21 which carries out signal processing of information obtained via the endoscope front-end unit portion 97, and a monitor 36 which displays an endoscope image based on an image signal which is generated by the processor unit 21.

Figure 2:
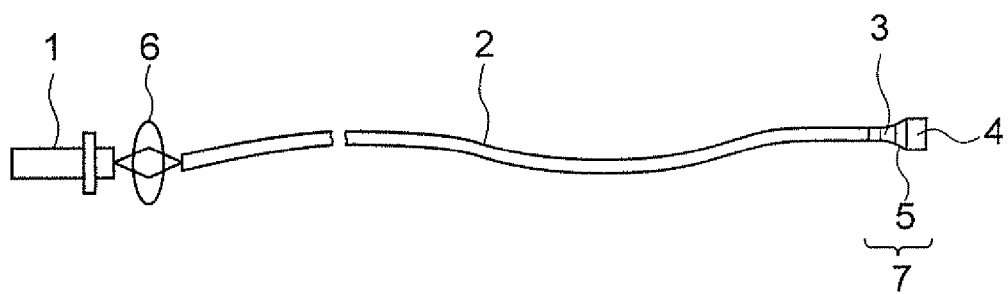
FIG. 2 is a diagram showing a structure of main components of the semiconductor light source apparatus.

Moreover, as shown in FIG. 2, the semiconductor light source apparatus of the first embodiment includes a light source 1, the optical fiber 2 which guides excitation light emitted from the light source 1, and the front-end unit portion 7. The front-end unit portion 7 has a wavelength converting member 4, a concave lens 3 which spreads the excitation light by a negative refracting power on the wavelength converting member 4, and a holding member 5 which holds the optical fiber 2, the concave lens 3, and the wavelength converting member 4.

The light source 1 is a semiconductor laser for exciting the wavelength converting member 4. In the first embodiment, an excitation wavelength of the semiconductor laser is 450 mm, and uses a blue-color semiconductor laser having a maximum output of 500 mW.

The optical fiber 2 is optically connected to the light source 1 via a lens 6. A multi-mode fiber having a numerical aperture NA of 0.4, a core diameter of 50 μm, and a cladding diameter of 125 μm can be used as the optical fiber 2.

The wavelength converting member 4 is a member in which a fluorescent substance is mixed in a resin. Here, the fluorescent substance is a material of which, electrons are excited from a ground level to an excitation level due to external factors in an energy level, and which emits light when the electrons return once again to the ground level. In the first embodiment, among such materials, a powder fluorescent substance is used. As an example of the powder fluorescent substance, a common fluorescent substance which emits light at a peak wavelength of 540 nm efficiently at the excitation wavelength of 450 nm, such as YAG:Ce can be used.

As the resin, a silicone resin which can withstand light of short wavelength, of a methyl type having a refractive index of 1.4 can be used.

Figure 3:
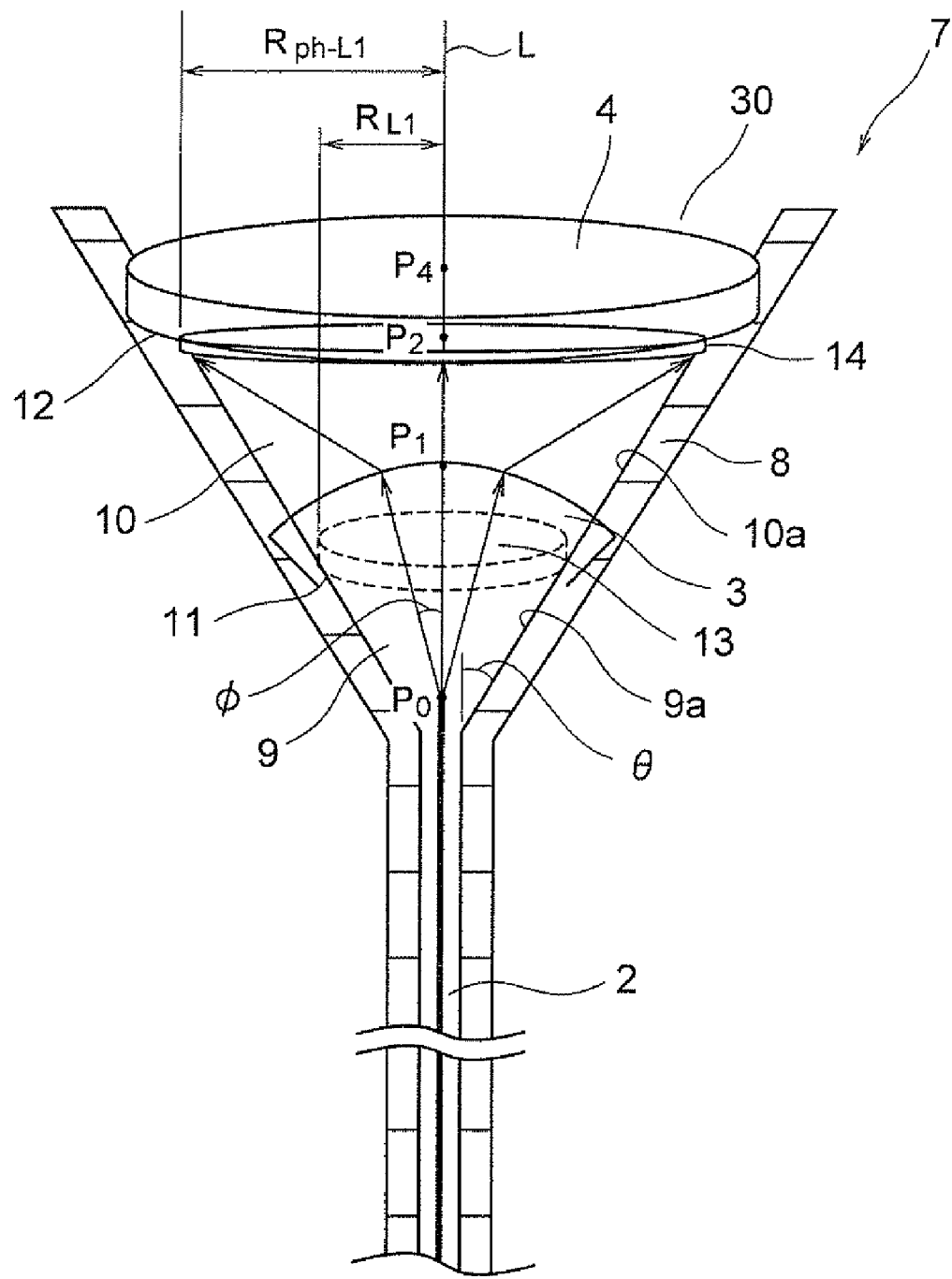
FIG. 3 is a diagram showing a cross-sectional view of a front-end unit portion in FIG. 2.
Figure 4:
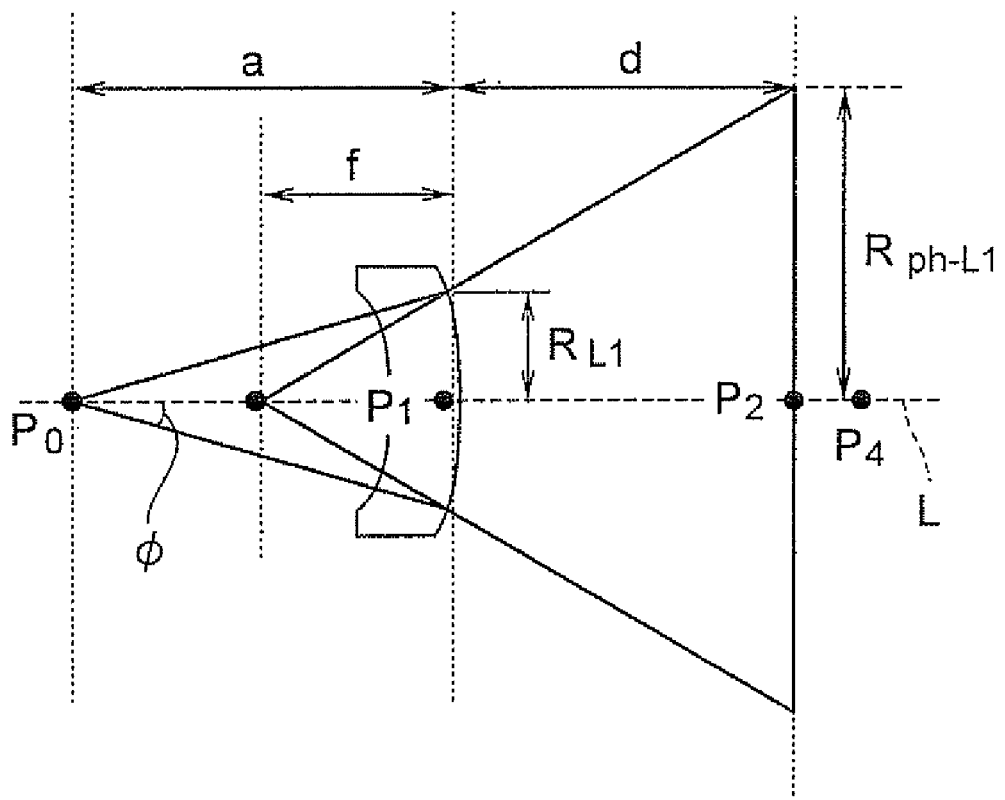
FIG. 4 is a diagram showing a positional relationship of an emitting end portion, a concave lens, and a wavelength converting member.
Figure 5:
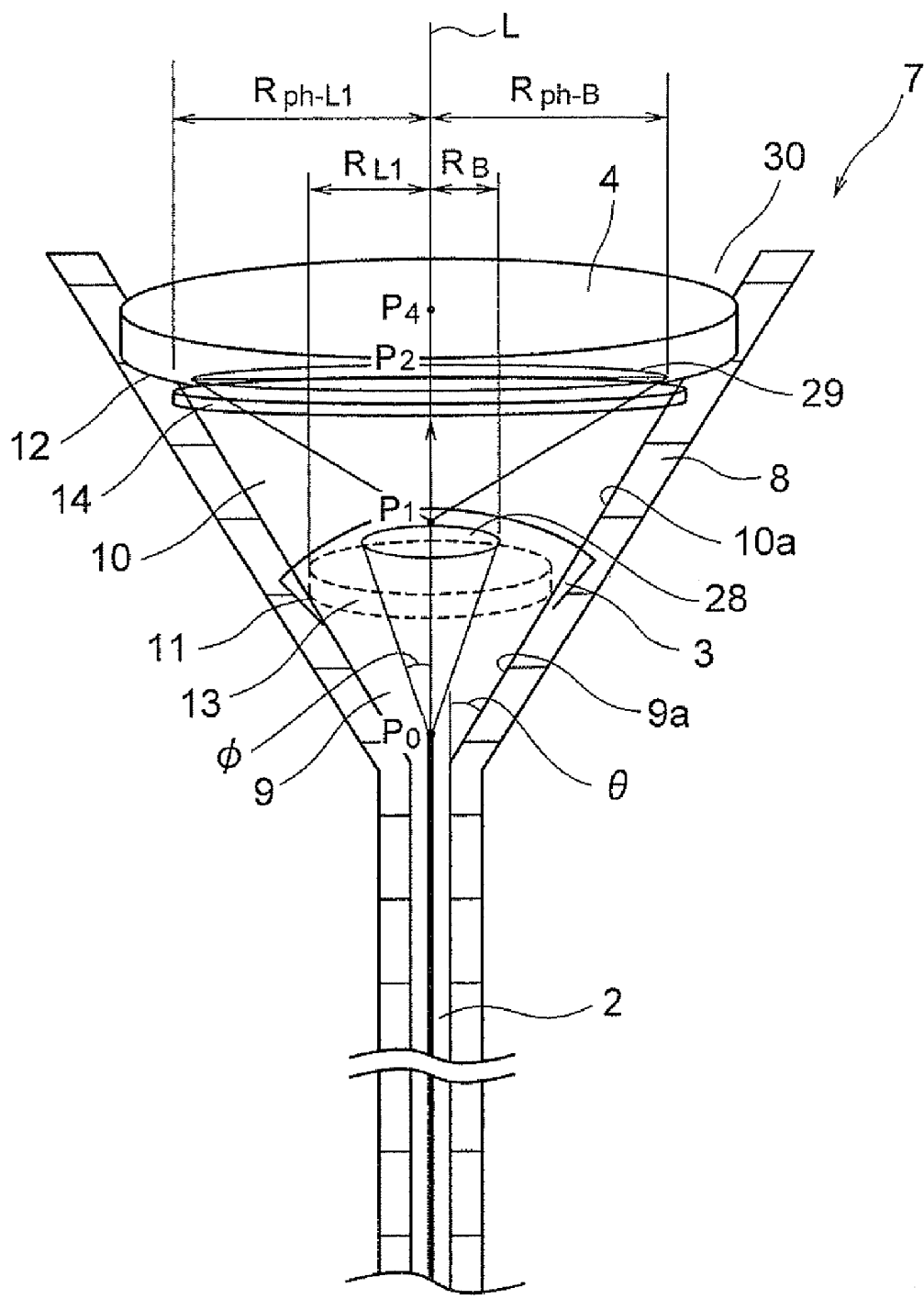
FIG. 5 is a diagram showing a beam spot of excitation light at each concave lens and the wavelength converting member.

Next, the front-end unit portion 7 will be described below by referring to diagrams from FIG. 3 to FIG. 5. FIG. 3 is a diagram showing a cross-sectional view of the front-end unit portion 7 in FIG. 2. FIG. 4 is a diagram showing a positional relationship of an emitting end portion Po, the concave lens 3, and the wavelength converting member 4. FIG. 5 is a diagram in which, a progress of a beam of the excitation light at each concave lens 3 and the wavelength converting member 4 is shown.

As shown in FIG. 3, in a cavity 30 which is at an interior portion of a holding member 8, the optical fiber 2, the concave lens 3, the wavelength converting member 4, a concave lens fixing portion 11, and a wavelength converting member fixing portion 12 are disposed at predetermined positions. The cavity 30 has a first cavity 9 and a second cavity 10.

The first cavity 9 which is an internal space between the optical fiber 2 and the concave lens 3 of the holding member 8 has a first taper surface 9a which is spread from a side where the optical fiber 2 is disposed, toward a side where the concave lens 3 is disposed.

A reflecting surface which reflects efficiently the excitation light from the excitation light source 1 is formed on the first taper surface 9a.

Moreover, the second cavity 10 which is an internal space between the concave lens 3 and the wavelength converting member 4 has a second taper surface 10a which is spread from a side where the concave lens 3 is disposed, toward a side where the wavelength converting member 4 is disposed. A side surface of the first cavity 9 (the first taper surface 9a) and a side surface of the second cavity 10 (the second taper surface 10a) inside the holding member 8 have the same taper angle $\theta$.

A reflecting surface which reflects efficiently the excitation light passed through the concave lens 3 and wavelength converted light having the wavelength converted by the wavelength converting member 4, is formed on the second taper surface 10a.

An angle of incidence $\phi$ of the excitation light emitted from the optical fiber 2 can be calculated based on the numerical aperture (NA) of the optical fiber 2. In other words, it is possible to calculate the angle of incidence $\phi$ by expression (1).

$$\phi = \sin^{-1}(NA) \quad (1)$$

The first taper surface 9a of a side surface of the first cavity 9 has substantially same or larger taper angle than the angle of incidence $\phi$ of the excitation light calculated by expression (1), and is structured such that the excitation light emitted from the emitting end portion Po of the optical fiber 2 is not irradiated directly to the first taper surface 9a.

An outer diameter of the concave lens 3 is formed to be substantially circular-shaped, and the concave lens 3 is disposed between the first cavity 9 and the second cavity 10 at the interior of the holding member 8. An area excluding a portion installed and held in a state of the concave lens 3 installed is let to be an effective area 13 of the concave lens 3. When a radius of the effective area 13 of the concave lens 3 inside the cavity 30 is let to be $R_{L1}$ and a distance between the optical fiber 2 and the concave lens 3 is let to be a, by letting a relation as shown in expression (2), it is possible to irradiate the excitation light efficiently to the effective area 13 of the concave lens 3.

$$R_{L1} \geq a \times \tan \phi \quad (2)$$

In other words, the effective area 13 of the concave lens 3 as shown in FIG. 5 is formed to be substantially same or larger as compared to a beam spot 28 of the excitation light formed on a diverging means (diverging unit).

For example, when the numerical aperture (NA) of the fiber is NA=0.4, according to expression (1), the angle of incidence $\phi$ of the excitation light emitted from the optical fiber 2 is 23.6°, and when the distance between the optical fiber 2 and the concave lens 3 is let to be 1 (mm), according to expression (2), the radius $R_{L1}$ of the effective area of the concave lens 3 is 0.44 mm or more. Here, the radius $R_{L1}$ of 0.44 (mm) is favorable. However, when the effective area 13 of the concave lens 3 is larger than a diameter of a beam spot of the excitation light, the excitation light can be used efficiently.

An outer diameter of the wavelength converting member 4 is formed to be substantially circular-shaped, and is disposed inside the holding member 8. Regarding a wavelength conversion characteristic of the wavelength converting member 4, the wavelength conversion characteristic of an outer peripheral portion might be degraded as compared to the wavelength conversion characteristic near a central portion due to issues in manufacturing. Therefore, an effective wavelength conversion area 14 of the wavelength converting member 4 is formed assuming to be circular shaped having a radius $R_{ph-L1}$ somewhat smaller than an outer diameter thereof. Normally, since degradation of characteristic of the outer peripheral portion is not that substantial, an area excluding an installing portion of the wavelength converting member 4 on the holding member 8 is let to be the effective wavelength conversion area 14.

A radius of the effective wavelength conversion area 14 of the wavelength converting member 4 is let to be $R_{ph-L1}$, a focal length of the concave lens 3 is let to be f, a distance between the emitting end portion Po of the optical fiber 2 and the concave lens 3 is let to be a, a distance between the concave lens 3 and the wavelength converting member 4 is let to be d, and the angle of incidence of the excitation light emitted from the optical fiber 2 is let to be $\phi$. In this case, an arrangement is made such that expression (3) is satisfied. Accordingly, it is possible to irradiate the excitation light spread by the concave lens 3 to the effective wavelength conversion area 14 of the wavelength converting member 4.

$$R_{ph-L1} \geq \tan \phi \{fa + d(f+a)\}/f \quad (3)$$

In other words, the effective wavelength conversion area 14 of the wavelength converting member 4 is formed to be substantially same or larger as compared to a beam spot 29 of the excitation light formed on the diverging unit (the wavelength converting member 4).

For example, when the focal length of the concave lens 3 is let to be 0.5 mm, the distance a between the emitting end portion Po of the optical fiber 2 and the concave lens 3 is let to be 1 (mm), the distance d between the concave lens 3 and the wavelength converting member 4 is let to be 1 (mm), and the angle of incidence $\phi$ of the excitation light emitted from the optical fiber 2 is let to be 23.6(°), the radius $R_{ph-L1}$ of the effective wavelength conversion area 14 of the wavelength converting member 4 according to expression (3) is 1.75 (mm).

The concave lens fixing portion 11 for fixing the concave lens 3 to the holding member 8 and the wavelength converting member fixing portion 12 for fixing the wavelength converting member 4 to the holding member 8, when viewed from a direction of a front end portion of the wavelength converting member 4, are circular-shaped grooves which fit in an inner surface of the holding member 8 having a circular conical shape, or fixed portions on which, small plate members are installed at an equal interval.

It is desirable that the effective area 13 of the concave lens 3 is substantially same with respect to (is same as) the beam spot 28 of the excitation light on the concave lens 3 in expression (2), and may be larger than that at a point where there is no loss of the excitation light. It is desirable that the radius $R_{L1-ph}$ ($R_{ph-L1}$) of the effective wavelength conversion area of the wavelength converting member 4 is substantially same with respect to the beam spot 29 of the excitation light on the wavelength conversion area 14 in expression (3), and may be larger than that at a point where there is no loss of the excitation light.

An operation of the semiconductor light source apparatus according to the first embodiment will be described below while referring to diagrams from FIG. 1 to FIG. 5. The excitation light emitted from the light source 1 is optically coupled with the optical fiber 2 via the lens 6, and is guided inside a core of the optical fiber 2, according to NA which is the numerical aperture of the optical fiber 2. The excitation light emitted from the emitting end portion Po of the optical fiber 2 is emitted at an angle according to NA which is the numerical aperture, and advances to the concave lens 3. Thereafter, the excitation light is diverged by the concave lens 3 which has a negative refracting power, and the excitation light which has passed through the concave lens 3 is irradiated toward the effective wavelength conversion area 14 of the wavelength converting member 4.

As shown in FIG. 3, the excitation light emitted from the emitting end portion Po of the optical fiber 2 advances upon being spread according to the NA of the optical fiber 2. Since the taper angle θ of the holding member 8 is a taper angle greater than the angle of incidence φ which is calculated from the NA of the optical fiber 2, the excitation light, basically, without being irradiated to the first taper surface 9a, advances toward the concave lens 3. However, due to bending and installing state of the optical fiber 2, sometimes, the excitation light is emitted at an angle greater than the angle of incidence calculated by the NA of the optical fiber 2, from the emitting end portion Po of the optical fiber 2. A part of such light is irradiated to the side surface of a cavity (the first taper surface 9a) of the holding member 8. However, since the side surface of the cavity is a reflecting surface, the light is reflected at the side surface of the cavity, and is irradiated to the wavelength converting member 4. As a result, it is possible to let to decrease, the loss of the excitation light due to the bending and installing state of the optical fiber 2.

As shown in FIG. 5, the beam spot 29, which the excitation light diverged by the concave lens 3 forms on the wavelength converting member 4, is irradiated to an area which is substantially same as the effective wavelength conversion area 14. In other words, when a radius of an effective area of the wavelength converting member 4 is let to be $R_{ph-L1}$ and a radius of the beam spot 29 on the wavelength converting member 4 is let to be $R_{ph-B}$, it is favorable that $R_{ph-L1} \geq R_{ph-B}$.

A part of the excitation light is absorbed by the wavelength converting member 4, and becomes wavelength-converted light upon being subjected to wavelength conversion. A part of the wavelength-converted light is emitted as light irradiated from a reflecting side of a surface to which the excitation light of the wavelength converting member 4 is irradiated, and another part of the wavelength-converted light is irradiated to inside of the second cavity 10 of the holding member 8 from a surface to which the excitation light has been irradiated. The wavelength-converted light subjected to wavelength conversion, upon being emitted to inside of the second cavity 10, by being reflected at the reflecting surface of the side surface inside the second cavity 10 of the holding member 8, the part of the wavelength-converted light upon passing through the wavelength converting member 4, is emitted from the emitting end portion.

Moreover, another part of the excitation light irradiated to the wavelength converting member 4 is reflected by the wavelength converting member 4, and is irradiated to inside of the second cavity 10 of the holding member 8 upon being scattered. The excitation light irradiated to inside of the second cavity 10 is reflected at a reflecting surface of the cavity side surface (second taper surface 10a), and the part of the excitation light is irradiated once again to the wavelength converting member 4. Consequently, it is structured that it is possible to reuse the excitation light which is reflected and scattered by the wavelength converting member 4.

In FIG. 3, $P_0$ is let to be a point of emitting end portion of the optical fiber 2, $P_1$ is let to be a central point of the concave lens 3, $P_2$ is let to be a central point of the cavity side (side of the emitting end portion Po) of the wavelength converting member 14, and $P_4$ is let to be a central point of an emitted side of the wavelength converting member 4. Points $P_0$, $P_1$, $P_2$, and $P_4$ in the structural diagram in FIG. 3 are positioned on principal axis L of the excitation light, and correspond to the respective points in FIG. 4. As shown in FIG. 4, the excitation light emitted from the emitting end portion Po of the optical fiber 2 positioned at point $P_0$ is emitted to have a range of angle φ according to the numerical aperture NA of the optical fiber 2 inside the first cavity 9, and advances to the effective area 13 of the concave lens 3. Thereafter, the excitation light is refracted inside the concave lens 3, and the excitation light which has passed through the point $P_1$ of the concave lens 3 advances inside the second cavity 10, and is diverged toward the effective wavelength conversion area 14 of the wavelength converting member 4. A part of the excitation light advances straight to the principal axis L, and is irradiated to the point $P_2$ which is a center of the effective wavelength conversion area 14 of the wavelength converting member 4.

By making an arrangement by interposing the concave lens 3 between the optical fiber 2 and the wavelength converting member 4, it is possible to shorten a distance between the emitting end portion Po of the optical fiber 2 and the wavelength converting member 4, and to irradiate the excitation light by diverging to the effective wavelength conversion area 14 of the wavelength converting member 4.

Here, when the emitting end portion Po of the optical fiber 2 and the wavelength converting member 4 are brought closer without interposing the diverging means in between, since intensity of the excitation light per unit area which is irradiated to the wavelength converting member 4 becomes increases, a temperature rises locally. As a result, given wavelength conversion characteristic of the wavelength converting member 4 and durability are considered to be degraded, and also a resin material is considered to be deteriorated.

Particularly, by the rise in temperature, a color of the resin is changed and then a light transmittance of the resin is degraded.

Correspondingly, in the first embodiment, since the concave lens 3 for spreading widening a spot diameter of the excitation light on the effective wavelength conversion area 14 of the wavelength converting member 4 is provided between the emitting end portion Po of the optical fiber 2 and the wavelength converting member 4, as a diverging means of the excitation light, it is possible to avoid such problem.

Furthermore, from a heat-resistant property of the resin and a temperature characteristic of the phosphor, by setting a size of the concave lens 3 and the wavelength converting member 4, and a positional relationship, or in other words, a distance between the emitting end portion Po of the optical fiber 2, concave lens 3, and the wavelength converting member 4 according to a guideline of the first embodiment, it is possible to use various resins and phosphors efficiently. Moreover, by setting the size of the concave lens 3 and the wavelength converting member 4 as mentioned above, it is possible to realize an efficient semiconductor light source apparatus.

In the first embodiment, the arrangement has been made such that the diameter of the beam spot 29 which the excitation light emitted from the optical fiber 2 forms on the wavelength converting member 4, and the diameter of the effective wavelength conversion area 14 of the wavelength converting member 4 are substantially same. However, the diameter of the beam spot 29 and the diameter of the effective wavelength conversion area 14 are not necessarily required to be the same. When the diameter of the beam spot 29 on the wavelength converting member 4 is substantially same as or smaller than the diameter of the effective wavelength conversion area 14, it can be said that the excitation light is used efficiently.

On the other hand, when the rise in temperature of the abovementioned wavelength converting member 4 is taken into consideration, it is very difficult to make the diameter of the beam spot 29 of the excitation light on the wavelength converting member 4 extremely small. Therefore, when the diameter of the effective wavelength conversion area 14 of the wavelength converting member 4 is made sufficiently large as compared to the diameter of the beam spot 29, the front-end unit portion 7 becomes large. In the arrangement of the first embodiment, when a ratio $S_s/S_{ph}$ of an area $S_{ph}$ of the effective wavelength conversion area 14 of the wavelength converting member 4 and an area $S_s$ of the beam spot of the excitation light formed on the wavelength converting member 4 is in a range of 0.25 to 1, it is possible to achieve with good balance both of a high efficiency of the excitation light and a downsizing of the front-end unit portion 7.

Furthermore, in the first embodiment, since an inner surface of the cavity of the holding member 8 is let to be a reflecting surface, it is possible to reuse a part of the excitation light and the wavelength-converted light irradiated directly or indirectly to the reflecting surface, and as a result, it is possible to make emit a bright illuminating light.

When the angle of incidence φ of the excitation light is wider than the taper angle θ of the holding member 8 structured as described above, the excitation light is irradiated to the first taper surface 9a and the second taper surface 10a. However, it is possible to reduce loss of the excitation light by preventing this.

It is possible to construct a high efficiency light source apparatus easily, by setting parameters of position and size of the emitting end portion Po of the optical fiber 2, the concave lens 3, and the wavelength converting member 4 easily, by determining one parameter according to relational expressions (2) and (3) of the focal length of the concave lens 3.

Modified Embodiment of First Embodiment

Figure 6:
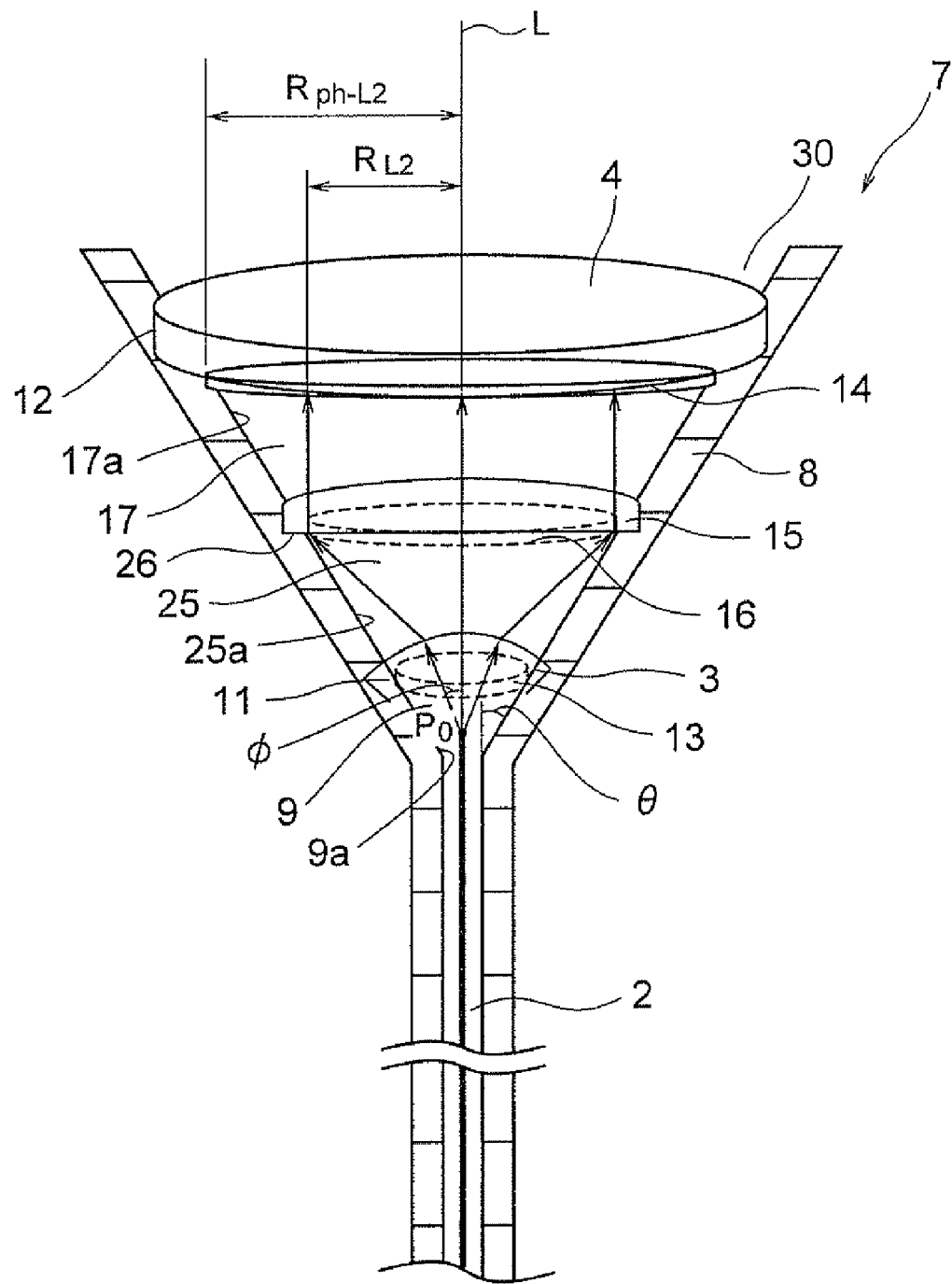
FIG. 6 is a diagram showing a cross-sectional view of the front-end unit portion.
Figure 7:
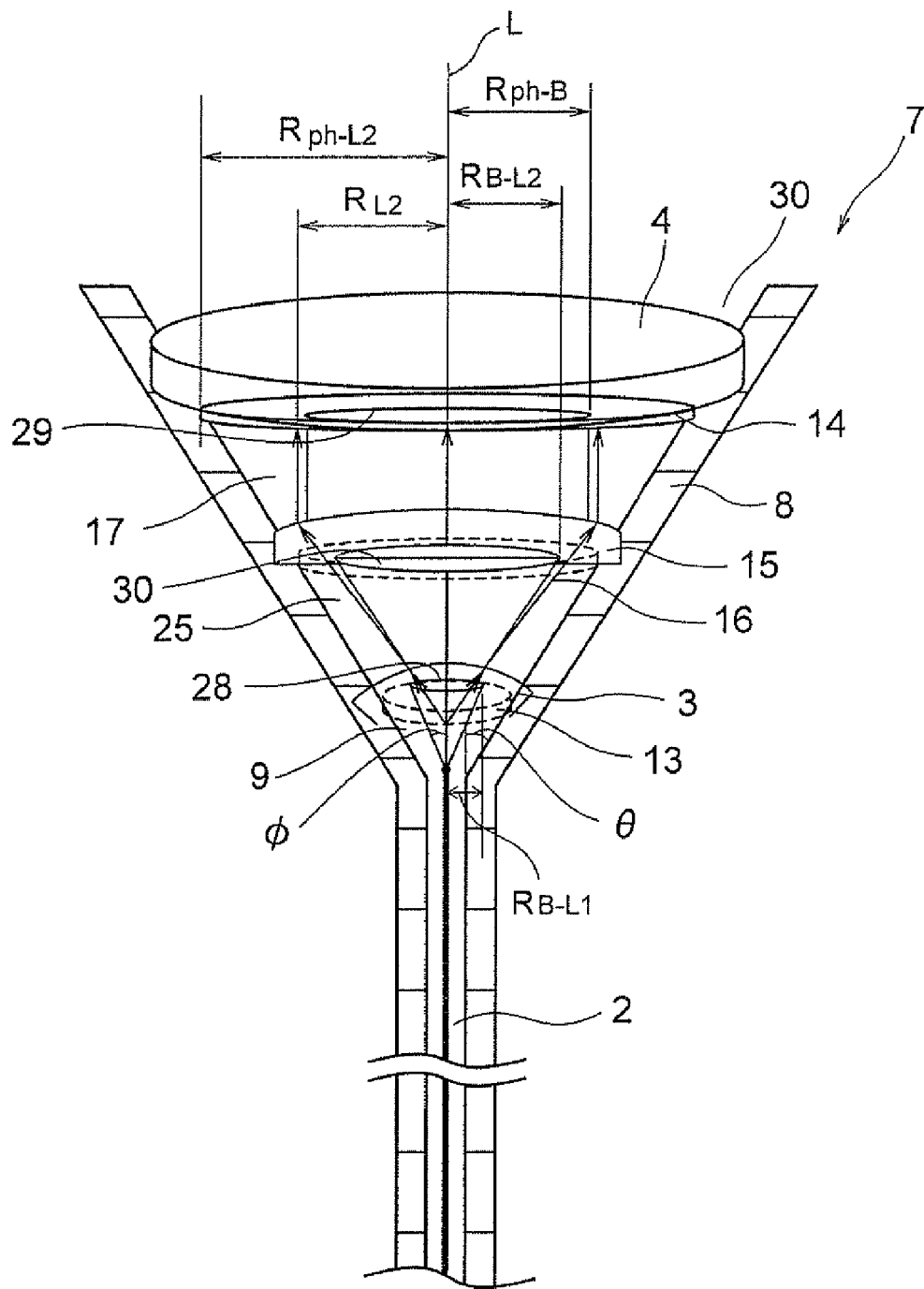
FIG. 7 is a diagram showing a beam spot of excitation light at each concave lens, convex lens, and the wavelength converting member.

A semiconductor light source apparatus of a modified embodiment of the first embodiment of the present invention will be described below while referring to FIG. 6 and FIG. 7. FIG. 6 is a diagram showing a cross-sectional structure (view) of the front-end unit portion 7, and FIG. 7 is a diagram in which, a beam spot of the excitation light at each of the concave lens 3, a convex lens 15, and the wavelength converting member 4 is shown. Firstly, a structure of the modified embodiment of the first embodiment will be described below.

In FIG. 6 and FIG. 7, members denoted by the same reference numerals as the members denoted in FIG. 3 which is a structural diagram of the first embodiment are similar members, and detail description thereof is omitted. At the interior of the holding member 8, in other words, inside the cavity 30, the optical fiber 2, the concave lens 3, the convex lens 15; the wavelength converting member 4, the concave lens fixing portion 11, a convex lens fixing portion 26, and the wavelength converting member fixing portion 12 are disposed at predetermined positions. A difference from the first embodiment shown in FIG. 3 is that the convex lens 15 and the concave lens 3 are combined at the interior of the holding member 8. The convex lens 15 is disposed in an area between the concave lens 2 and the wavelength converting member 4. The cavity 30 has the first cavity 9, a second cavity 25, and a third cavity 17.

The first taper surface 9a of the side surface of the first cavity 9 has a taper angle θ which is substantially same as or larger than an angle of incidence φ of the excitation light, and an arrangement is made such that the excitation light emitted from the emitting end portion Po of the optical fiber 2 is not irradiated directly to the first taper surface 9a. A reflecting surface which reflects efficiently the excitation light from an excitation light source 1 is formed on the first taper surface 9a.

Moreover, the second cavity 25 which is an internal space between the concave lens 3 and the convex lens 15 has a second taper surface 25 which is spread from the side where the concave lens 3 is disposed, toward a side where the convex lens 15 is disposed. A reflecting surface which reflects efficiently the excitation light which is spread upon passing through the concave lens 3 and the excitation light which is subjected to total reflection at the surface of the concave lens 3 is formed on the second taper surface 25a.

The third cavity 17 which is an internal space between the convex lens 15 and the wavelength converting member 4 has a third taper surface 17a which is spread from the side where the convex lens 15 is disposed, toward a side where the wavelength converting member 4 is disposed. A reflecting surface which reflects efficiently the excitation light which has passed through the convex lens 15 and wavelength-converted light which is subjected to wavelength conversion by the wavelength converting member 4 are reflected, is formed on the third taper surface 17a. The side surface of the second cavity 25 (the second taper surface 25a) and the first cavity 9 and a side surface of the third cavity 17 (third taper surface 17a) inside the holding member 8 have a similar taper angle θ.

An outer diameter of the convex lens 15 is formed to be substantially circular-shaped, and the convex lens 15 is disposed between the third cavity 25 and the second cavity 17 at the interior of the holding member 8. An area excluding a portion installed and held in a state of the convex lens 15 installed is let to be an effective area 16 of the convex lens 15. The effective area 16 of the convex lens 15 is formed as a circular shape smaller than the outer diameter of the convex lens 15. as shown in FIG. 7, when a radius of the effective area of the convex lens 15 inside the cavity 10 is let to be substantially same as or larger than a diameter of a beam spot 30 on the convex lens 15. In other words, when the radius of the effective area 16 of the convex lens 15 is let to be $R_{L2}$, and the radius of the beam spot 30 on the convex lens 15 is let to be $R_{B-L2}$, it is arranged to satisfy $R_{L2} \geq R_{B-L2}$.

An arrangement is made such that the effective wavelength conversion area 14 of the wavelength converting member 4 is substantially same as or larger than the effective area 16 of the convex lens 15 which makes light which is diverged at the concave lens 3, to be parallel light beam.

The convex lens fixing portion 26, when viewed from a direction of front end portion of the wavelength converting member 4, is a circular-shaped groove which fits on the inner surface of the holding member 8 having a circular conical shape, or a fixed portion on which, small plate members are installed at an equal interval.

It is desirable that the radius $R_{L2}$ of the effective area 16 of the convex lens 15 is same as a size of the diameter of the concave lens 3, and may be larger than the size of the diameter of the concave lens 3, at a point where there is no loss of the excitation light.

Next, An operation of the present modified embodiment of the first embodiment will be described below while referring to FIG. 6 and FIG. 7.

The excitation light emitted from the emitting end portion Po of the optical fiber 2 advances while spreading according to the NA of the optical fiber 2. Since the taper angle θ of the holding member 8 is wider than an angle of incidence φ which is calculated from the NA of the optical fiber 2 by using the abovementioned expression (1), the excitation light, basically, advances toward the concave lens 3 without being irradiated to the first taper surface 9a. A portion of the excitation light diverged by the concave lens 3 is incident on the convex lens 15, and the excitation light, upon being refracted inside the convex lens 15, is irradiated as a substantial parallel light to the effective wavelength conversion area 14 of the wavelength converting member 4. As shown in FIG. 7, the beam spot 29 of the excitation light formed on the wavelength converting member 4 is irradiated to an area same as or smaller than the effective wavelength conversion area 14.

A part of the excitation light is absorbed by the wavelength converting member 4, and becomes a wavelength-converted light upon being subjected to wavelength conversion. A part of the wavelength-converted light is emitted as light irradiated from a reflecting side of a surface to which the excitation light of the wavelength converting member 4 is irradiated, and another part of the wavelength-converted light is irradiated to inside of the third cavity 17 of the holding member 8 from a surface to which the excitation light has been irradiated. The wavelength-converted light upon being emitted to inside of the third cavity 17 being reflected at the reflecting surface of the side surface inside the third cavity 17 (third cavity surface 17a) of the holding member 8, the part of the wavelength-converted light upon passing through the wavelength converting member 4, is emitted from the emitting end portion.

Moreover, a part of the excitation light irradiated to the wavelength converting member 4 upon being reflected and scattered by the wavelength converting member 4, is irradiated to the inside of the third cavity 17 of the holding member 8. The excitation light reflected and scattered to the inside of the third cavity 17 is reflected at the side surface of the cavity (the second taper surface 17a), and the part of the excitation light is irradiated once again to the wavelength converting member 4. Consequently, it is possible to exit outside a part of the excitation light which is reflected and scattered by the wavelength converting member 4.

By making an arrangement as mentioned above, since it is possible to irradiate parallel light passed through the convex lens 15 to the effective wavelength conversion area 14 of the wavelength converting member 4, with a power density more uniform than a power density in the first embodiment, it is possible to reduce unevenness in color of the emitted light.

Furthermore, in the modified embodiment of the first embodiment, by converting to parallel light inside the third cavity 17 inside the holding member 8, it is possible to reduce reflection of the excitation light at the third taper surface 17a. By preventing such reflection, it is possible to reduce the loss of excitation light, and to irradiate the excitation light to the effective wavelength conversion area 14 of the wavelength converting member 4.

Moreover, by letting a surface inside the holding member to be a taper surface, it is possible to achieve a light source which can be used even in an endoscope in which, irradiated light emitting portion is made small-sized.

Second Embodiment

Figure 8:
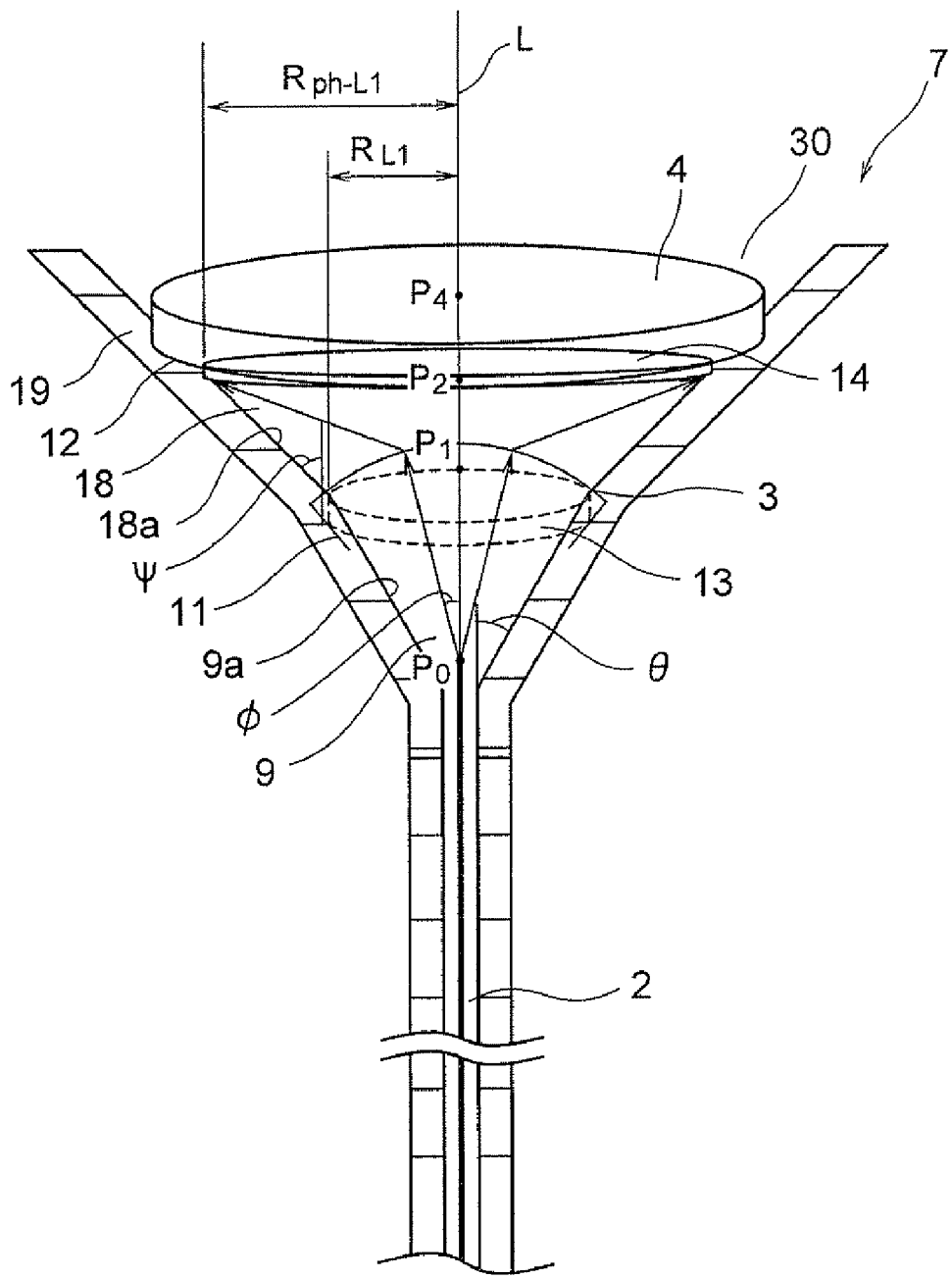
FIG. 8 is a diagram showing a cross-sectional view of a front-end unit portion 7 of a semiconductor light source apparatus according to a second embodiment.

A semiconductor light source apparatus according to a second embodiment of the present invention will be described below while referring to FIG. 8. FIG. 8 is a diagram showing a cross-sectional view of the front-end unit portion 7 of the semiconductor light source apparatus according to the second embodiment. The second embodiment differs from the first embodiment at a point that, a holding member 19 of the front-end unit portion 7 provided at a side of the emitting end portion Po of the optical fiber 2 is structured in which a taper inclination angle of the holding member 19 differs partially as shown in FIG. 8.

In FIG. 8, members denoted by same reference numerals as the members shown in FIG. 3 of the first embodiment are similar, and detail description thereof is omitted.

At interior of the holding member 19, in other words, inside the cavity 30, the optical fiber 2, the concave lens 3, the wavelength converting member 4, the concave lens fixing portion 11, the wavelength converting member fixing portion 12, are disposed at predetermined positions. The holding member shown in FIG. 8 is formed of the holding member 19 which is tapered, having two different taper angles namely, a first taper angle θ, and a second taper angle ψ which is larger than the first taper angle θ. The cavity 30 has the first cavity 9 and a second cavity 18.

The first cavity 9 which is an internal space between the emitting end Po of the optical fiber 2 and the concave lens 3 of the holding member 19 has a first taper angle θ which is spread from the side of the emitting end of Po of the optical fiber 2 toward the concave lens 3. A reflecting surface which reflects efficiently the excitation light from the excitation light source 1 is formed on the first taper surface 9a.

Moreover, the second cavity 18 which is an internal space between the concave lens 3 and the wavelength converting member 4 has a taper angle 41 which is spread from the side of the concave lens 3 toward the side where the wavelength converting member 4. A reflecting surface which reflects efficiently the excitation light passed through the concave lens 3, and the wavelength-converted light which is subjected to wavelength conversion by the wavelength converting member 4 is formed on the second taper surface 18a.

It is possible to calculate an angle of incidence φ of the excitation light emitted from the optical fiber 2, from the NA which is the numerical aperture of the optical fiber 2. In other words, it is possible to determine the angle of incidence φ by the abovementioned expression (1)

$$\phi = \sin^{-1}(NA) \quad (1)$$

The first taper angle θ of the side surface of the first cavity 9 (the first taper surface 9a) is substantially same as or greater than the angle of incidence φ of the excitation light, and the first taper surface 9a is formed such that the excitation light emitted from the emitting end portion Po of the optical fiber 2 is not irradiated directly to the first taper surface 9a.

The outer diameter of the concave lens 3 is formed to be substantially circular-shaped, and is disposed between the first cavity 9 and the second cavity 18 at the interior of the holding member 19. An area excluding a portion installed and held in a state of the concave lens 3 installed is let to be the effective area 13 of the concave lens 3. When the radius of the effective area 13 of the concave lens 3 is let to be $R_{L1}$, and the distance between the optical fiber 2 and the concave lens 3 is let to be a, by making an arrangement such that the relation satisfies the abovementioned expression (2), it is possible to irradiate efficiently, the excitation light spread by the concave lens 3 to the effective area 13 of the concave lens 3.

$$R_{L1} \geq a \times \tan\phi \quad (2)$$

The second taper angle ψ of the side surface of the second cavity 18 (the second taper surface 18a) is same as or greater than an divergence angle of the excitation light which has passed through the concave lens 3, and (the second taper surface 18a) is formed such that the excitation light which is diverged is not irradiated directly to the second taper surface 18a.

The outer diameter of the wavelength converting member 4 is formed to be substantially circular-shaped, and is disposed in the cavity 30 inside the holding member 19. Regarding the wavelength conversion characteristic of the wavelength converting member 4, the wavelength conversion characteristic of the outer peripheral portion might be degraded as compared to the wavelength conversion characteristic near the central portion due to issues in manufacturing. Therefore, the effective wavelength conversion area 14 of the wavelength converting member 4 is formed assuming to be circular shaped having a radius $R_{ph-L1}$ somewhat smaller than the outer shape thereof. Normally, since degradation of characteristic of the outer peripheral portion is not that substantial, an area excluding an installing portion of the wavelength converting member 4 on the holding member 19 is let to be the effective wavelength conversion area 14.

An arrangement is made such that the diameter of the effective wavelength conversion area 14 of the wavelength converting member 4 substantially same or larger as compared to the diameter of the beam spot 29 of the excitation light on the wavelength conversion member 4, diverged upon passing through the concave lens 3. In other words, when the diameter of the effective area of the wavelength converting member 4 is let to be $R_{ph-L1}$, and the radius of the beam spot 29 on the wavelength converting member 4 is let to be $R_{ph-B}$, it is favorable that $R_{ph-L1} \geq R_{ph-B}$.

An operation of the second embodiment will be described below while referring to FIG. 4 and FIG. 8.

The excitation light emitted from the emitting end portion Po of the optical fiber 2 advances while spreading according to the NA of the optical fiber 2. Since the first taper angle θ of the side surface of the first cavity 9 of the holding member 19 between the emitting end portion Po of the optical fiber 2 and the concave lens 3 is greater than the angle of incidence φ which is calculated from the NA of the optical fiber 2, the excitation light, basically, without being irradiated to the first taper surface 9a, advances toward the concave lens 3.

Here, due to the bending and installing state of the optical fiber 2, sometimes, the excitation light is emitted at an angle greater than the angle of incidence φ calculated from the NA of the optical fiber 2, from the emitting end portion Po of the optical fiber 2. A part of such light is irradiated to the side surface of the first cavity 9 (the first taper surface 9a). In the second embodiment, the side surface of the first cavity 9 is a reflecting surface. Therefore, the light is irradiated toward the concave lens 3. It is possible to minimize the loss of excitation light due to such bending and installing state of the optical fiber 2.

The excitation light diverged by the concave lens 3 is irradiated to an area substantially same as or smaller than the effective wavelength conversion area 14 of the wavelength converting member 4. A part of the excitation light is absorbed by the wavelength converting member 4, and becomes a wavelength-converted light upon being subjected to wavelength conversion. A part of the wavelength-converted light is emitted as light irradiated from the reflecting side of the surface to which the excitation light of the wavelength converting member 4 is irradiated, and another part of the wavelength-converted light is irradiated to the inside of the second cavity 18 of the holding member 19 from a surface to which the excitation light has been irradiated. The wavelength-converted light upon being emitted to the inside of the second cavity 18 by being reflected at the reflecting surface of the side surface of the second cavity 18 (the second taper surface 18a), the part of the wavelength-converted light upon passing through the wavelength converting member 4, is emitted from an emitting end portion $P_4$ upon being passed through the wavelength converting member 4.

Moreover, a portion of the excitation light irradiated to the wavelength converting member 4 upon being reflected and scattered by the wavelength-converting member 4, is irradiated to the inside of the second cavity 18 of the holding member 19. The second taper angle ψ of the inside of the second cavity 18 is formed to be greater as compared to the first embodiment, such that the excitation light is not reflected directly. Therefore, the excitation light irradiated to the inside of the second cavity 18 is reflected at the reflecting surface of the side surface of the second cavity 18, and a part of the excitation light irradiated once again to the wavelength converting member 4 is irradiated toward a side of emitting end portion $P_4$ much more light as compared to the first embodiment, inside the second cavity 18.

In FIG. 8, $P_0$ is let to be a point of emitting end portion of the optical fiber 2, $P_1$ is let to be a central point of the concave lens 3, and $P_2$ is let to be a central point of the cavity side (side of the emitting end portion $P_0$) of the circular-shaped wavelength conversion area 14 of the wavelength converting member 4, and $P_4$ is let to be a central point of an emitting side of the wavelength converting member 4. Points $P_0$, $P_1$, $P_2$, and $P_4$ in the structural diagram in FIG. 8 are positioned on the principal axis L of the excitation light, and correspond to the respective points in FIG. 4. The excitation light emitted from the emitting end portion Po of the optical fiber 2 positioned at point $P_0$ is emitted to have a range of angle φ according to the numerical aperture NA of the optical fiber inside the first cavity 9, and advances to the effective area 13 of the concave lens 3. Thereafter, the excitation light is refracted inside the concave lens 3, and the excitation light which has passed through the point $P_1$ of the concave lens 3 advances inside the second cavity 18, and is diverged toward the effective wavelength conversion area 14 of the wavelength converting member 4. A part of the excitation light advances straight to the principal axis L, and is irradiated to the point $P_2$ which is a center of the effective wavelength conversion area 14 of the wavelength converting member 4.

By making the abovementioned arrangement, it is possible to achieve following effects;

Namely, since the second taper angle ψ of the second cavity 18 between the concave lens 3 and the wavelength converting member 4 is greater than in the first embodiment, it is possible to prevent the loss of excitation light reflected at the reflecting surface. Furthermore, when the second taper angle ψ is wide, the light subjected to wavelength conversion at the wavelength conversion area 14 of the wavelength converting member 4 is reflected at the second taper surface (reflecting surface) 18a, and it is possible to reuse that much amount of light.

Third Embodiment

Figure 9:
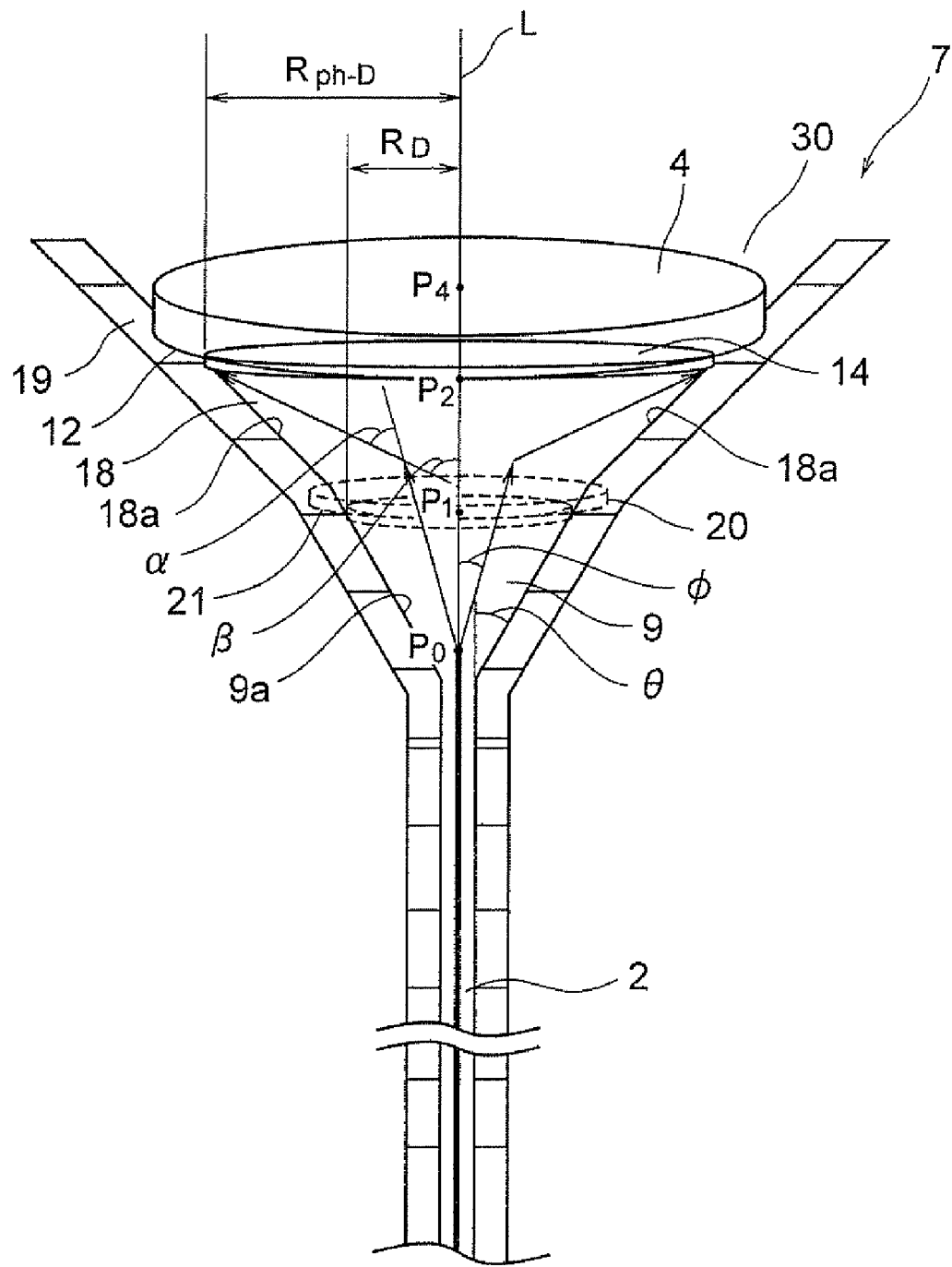
FIG. 9 is a diagram showing a cross-sectional view of the front-end unit portion 7 of a third embodiment.
Figure 10:
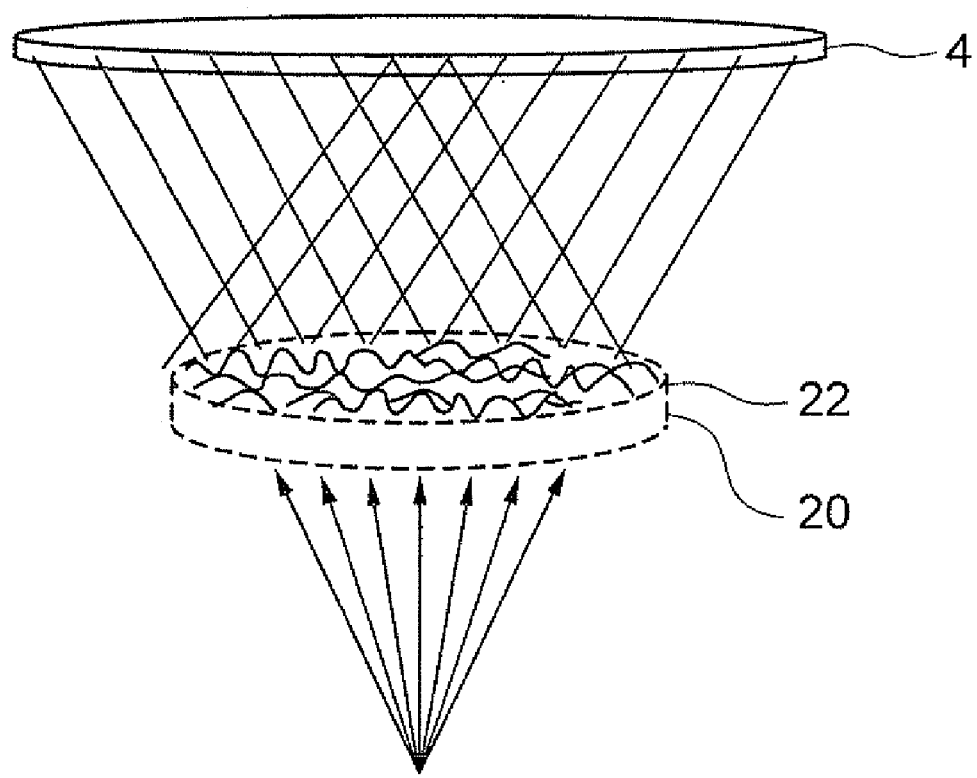
FIG. 10 is an enlarged perspective view of a structure of a concavo-convex surface of a plate member.
Figure 11:
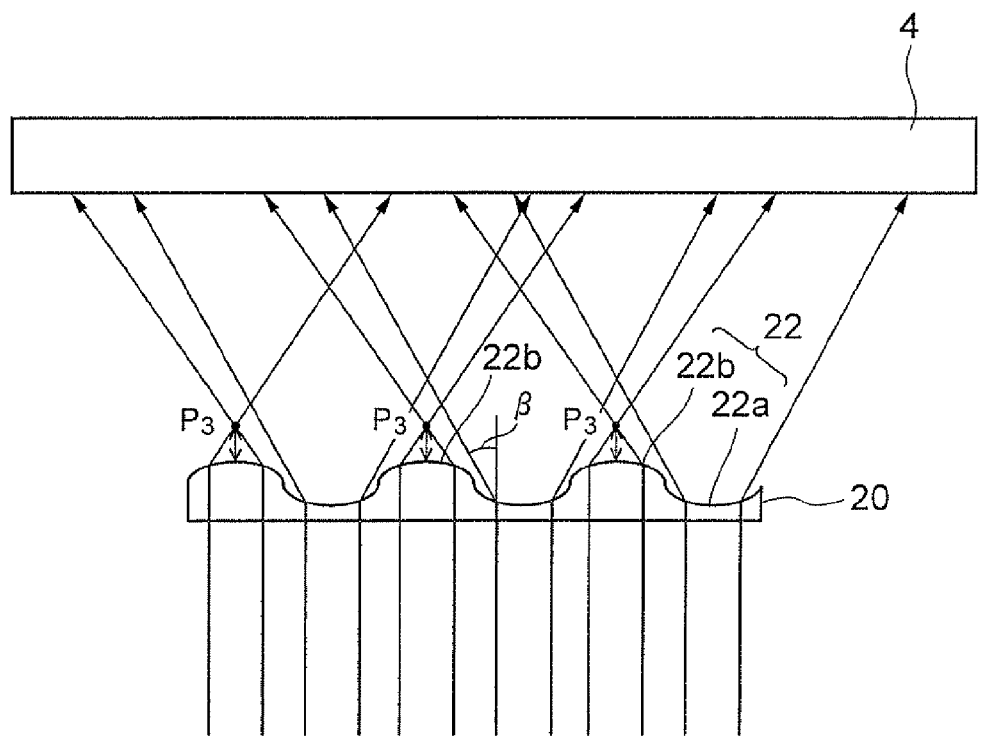
FIG. 11 is a diagram showing a cross-sectional view of the concavo-convex surface of the plate member.
Figure 12:
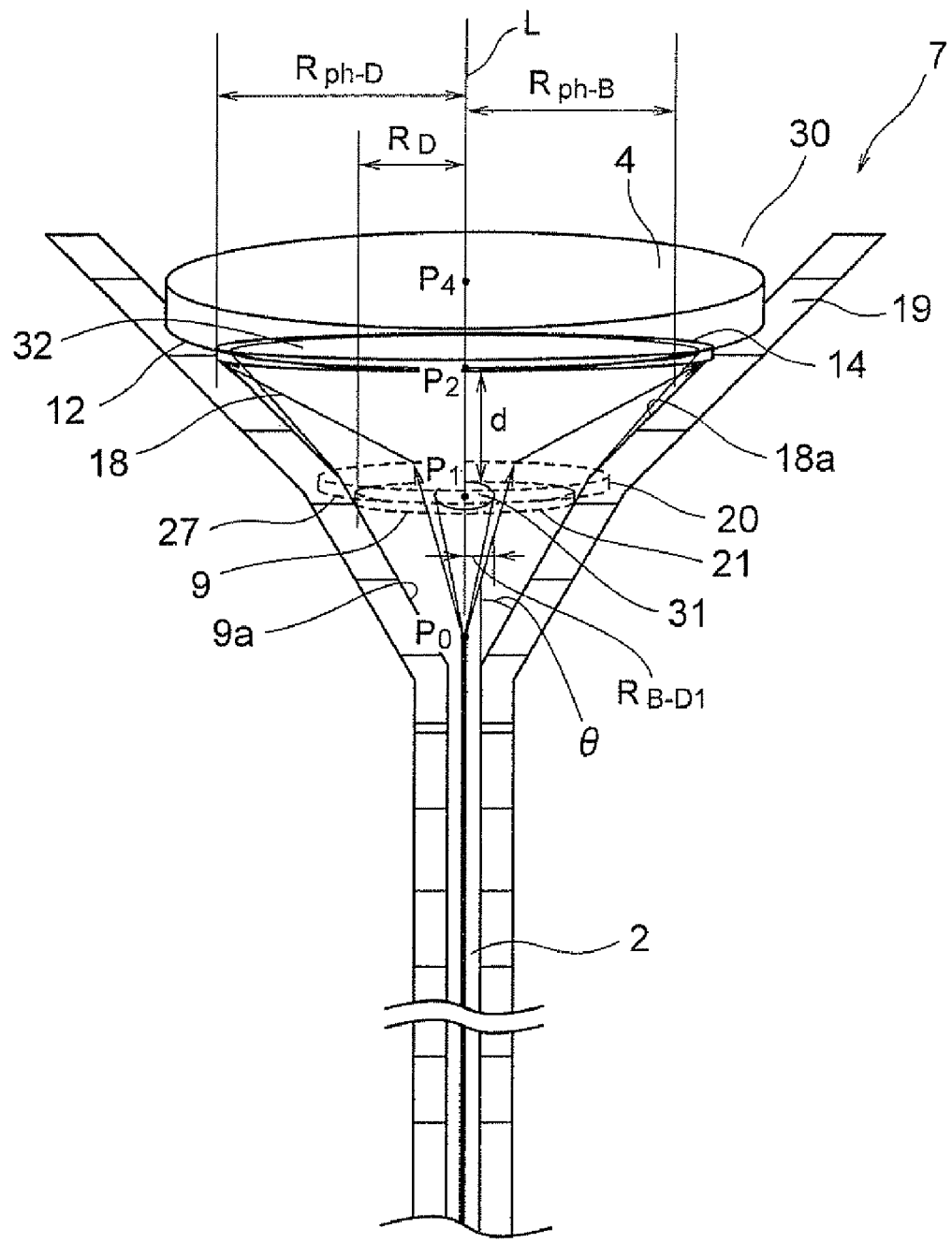
FIG. 12 is a diagram showing a beam spot of excitation light at the plate member and the wavelength converting member.

A semiconductor light source apparatus according to a third embodiment will be described below while referring to diagrams from FIG. 9 to FIG. 12. FIG. 9 is a diagram showing a cross-sectional view of the front-end unit portion 7 of the third embodiment. FIG. 10 is an enlarged perspective view showing a structure of a concavo-convex surface 22 of a plate member 20. FIG. 11 is a diagram showing a cross-sectional view of the plate member 20, and FIG. 12 is a diagram showing a beam spot of excitation light at the plate member 20 and the wavelength converting member 4.

The third embodiment differs from the first embodiment and the second embodiment at a point that the front-end unit 7 provided at a side of the emitting end portion Po of the optical fiber 2 is structured as shown in FIG. 9. In FIG. 9, members denoted by the same reference numerals as the members denoted in FIG. 3 are similar members, and detail description thereof is omitted.

The plate member 20 of FIG. 9, as shown in FIG. 10 and FIG. 11, has a pattern of a structure having extremely small recesses and projections formed on a surface thereof, disposed randomly. Each of the concave portion and convex portion has an effect of lens to the excitation light. Since a size of the concave portion and convex portion of a concavo-convex surface 22 is minute, a focal length of the concave portion and convex portion which is treated as a lens is minute. As shown in FIG. 11, if the convex portion is treated as a minute convex lens 22b, a focal length $P_3$ of a convex lens 22b is minute. That is to say, the concavo-convex surface 22 has a negative refracting power.

Namely, if a light is incident on the minute concave portion and convex portion, the light is advanced as below:

If the excitation light is incident on the minute concave portion 22a, the concave portion 22a is functioned as a concave lens. Therefore, the excitation light is diverged and is advanced.

Furthermore, if the excitation light is incident on the minute convex portion 22b, the convex portion 22b is functioned as a convex lens. A focal length $P_3$ of the convex lens is minute compared to an interval between the plate member 20 and the wavelength converting member 4. Therefore, the excitation light is once focused, and then is further advanced. Then, the excitation light is diverged and is advanced.

Consequently, a range of laser irradiated to the wavelength converting member 4 is widened.

Since the concave portion and convex portion 22 on the surface of the plate member 20 are disposed at random in its distance and its size, the concave portion and convex portion 22 diffuses the excitation light which is incident on the plate member 20 at random. Therefore, it is possible to make irradiation intensity uniform of the excitation light being incident on the wavelength converting member 4.

For example, the concavo-convex surface 22 is formed of a set of concave portion 22a and a convex portion 22b. Regarding the plate member 20 in the present embodiment, a difference in a height of the convex portion 22b and a height of the concave portion 22a is let to be in a range of 10 μm to 100 μm, and the interval between each other is the same order. Accordingly, the focal length $P_3$ is also of a micron order. Therefore, the plate member on which the concave portions 22a and the convex portions 22b are disposed at random has a diverging effect by refracting action as in a micro concave lens array. Here, an example in FIG. 11, an angle of incidence of the excitation light which has advanced from a lower side is let to be parallel light, is cited. However, since an angle of incidence of the excitation light of actual laser includes light having an angle other than an angle of the parallel light, the same argument is worked out.

Moreover, in the third embodiment, the plate member 20 in the form of a thin film of about 0.3 mm is used. Furthermore, if a resistance characteristic against a short-wavelength light is necessary for the plate member 20, it is possible to use materials such as a resin and glass etc. having a light resistance.

If a resin of which transmittance is in a range of 85% to 90% is used, and unlike a general diffusion plate, a loss of laser light could be minimized. The plate member 20 is formed to have a substantially circular-shaped outer diameter, and is disposed inside a frame member 19. An effective area 21 of the plate member 20 is formed as a circular area excluding a portion which is attached and held to the holding member 19.

The plate member 20 is structured to be an area substantially same as or wider than a circular-shaped effective area of the plate member 20 for irradiating the excitation light efficiently to the irradiated portion.

When this is indicated by a calculating expression, when a distance from the emitting end portion Po of the optical fiber 2 up to the plate member 20 is let to be a, the numerical aperture of the optical fiber 20 is let to be NA, an angle of incidence of the excitation light emitted from the light source is let to be $\phi(=\sin^{-1} NA \ldots (1))$, and a radius of a beam spot 31 on the plate member 20 is let to be $R_0$, an arrangement is made such that the relation satisfies the following expression (4). Accordingly, it is possible irradiate the excitation light efficiently to the effective area 21 of the plate member 20.

$$R_D \geq a \times \tan \phi \quad (4)$$

For example, when the numerical aperture of the optical fiber 2 is let to be NA=0.4, and the distance from the emitting end portion of the optical fiber 2 up to the plate member 20 is let to be 1 mm, the radius $R_D$ of the effective area 21 of the plate member 20 is approximately 0.44 mm. In this case, $R_D$ of 0.44 mm or rather larger is desirable. However, when the effective area 21 of the plate member 20 is larger than the beam spot 31 of the excitation light on the plate member 20, it is considered that the excitation light is used efficiently.

The beam spot 22 of the excitation light on the wavelength converting member 4 is calculated based on a distance between the plate member 20 and the wavelength converting member 4, the effective area 21 of the plate member 20, and a divergence angle α of the excitation light by the plate member 20.

In the present embodiment, an arrangement is made such that the effective wavelength conversion area 14 of the wavelength converting member 4 is an area substantially same as or larger than a beam spot 32 of the excitation light on the wavelength converting member 4. In other words, when a radius of the effective area 14 of the wavelength converting member 4 is let to be $R_{ph-D}$, and a radius of the beam spot 32 on the wavelength converting member 4 is let to be $R_{ph-B}$, it is structured to satisfy $R_{ph-D} \geq R_{ph-B}$.

As shown in FIG. 12, When the distance between the plate member 20 and the wavelength converting member 4 is let to be d, a radius of the plate member 20 is let to be $R_D$, the angle of incidence of the excitation light emitted from the light source and emitted from the emitting end portion $P_0$ is let to be $\phi(=\sin^{-1} NA \ldots (1))$, and the divergence angle of the excitation light by the plate member 20 when the excitation light is parallel light beam is let to be α, a spread angle of the light passed the plate member 4 when a light having angle of incidence φ, is let to be $\beta(=(\phi^2+\alpha^2)^{1/2})$, and the radius of the effective wavelength conversion area 14 of the wavelength converting member 4 is let to be $R_{ph-D}$. Here, the divergence angle α of the plate member 20 is an angle made by the principal axis of the excitation light, and a direction of divergence for which the intensity of light is half value of the maximum intensity of the light diverged on the principal axis of the excitation light, when the excitation light is incident as parallel light. Moreover, the spread angle β is an angle made by the principal axis of the excitation light, and a direction of divergence for which the intensity of light is half value of the maximum intensity of the light diverged on the principal axis of the excitation light, when the excitation light is incident on the plate member 20 at the angle of incidence φ.

Using above notation, a relational expression of a size of a beam spot 32 of the excitation light on the wavelength converting member 4, and the effective wavelength conversion area 14 on the wavelength converting member 4 is indicated in expression (5). By satisfying the expression (5), it is possible to irradiate efficiently the excitation light spread by the plate member 20 to the effective wavelength conversion area 14 of the wavelength converting member 4.

$$R_{ph-D} \geq R_D + d \times \tan \beta \qquad (5)$$

For example, when the numerical aperture of the optical fiber 2 is let to be NA=0.4, the distance d from the emitting end portion Po of the optical fiber 2 up to the plate member 20 is let to be 1 mm, the radius $R_D$ of the effective area 21 of the plate member 20 is let to be 0.44 mm, and the divergence angle α of the plate member 20 is let to be 20°, a radius $R_{ph-D}$ of the effective area 21 of the plate member 20 is approximately 1.04 mm or more. The effective area 21 of the plate member 20, radius 1.04 mm is desirable. If it is larger than the radius $R_{ph-B}$ of the beam spot 32 of the excitation light on the wavelength converting member 4, it can be said that the excitation light is used efficiently.

Further, as shown in the expression (4), It is desirable that the radius $R_D$ of the effective area 21 of the plate member 20 is substantially same as the beam spot 31, and may be larger than that at a point where there is no loss of excitation light.

It is favorable that the radius $R_{ph-D}$ of the effective wavelength conversion area 14 of the wavelength converting member 4 is same as the beam spot 32 of the excitation light on the wavelength conversion area 14 in expression (5), and may be larger than that at a point where there is no loss of excitation light.

It is possible to form the concavo-convex surface 22 by a method such as nano imprinting in which, a resin etc. is applied to a transparent substrate for the excitation light such as glass and resin, and upon bringing a formed mold in contact with the substrate, the structure is hardened by ultraviolet light, and then pattern transfer is carried out. Moreover, a method of molding a pattern by using sol-gel is also available. Furthermore, it is possible to form minute concave and convex portions directly on a surface of glass etc. In this case, for realizing the desired divergence angle α, the difference in the height of the concave portion 22a of the concavo-convex surface 22 and the height of the convex portion 22b of the concavo-convex surface 22 and the distance between a certain convex portion 22b and the adjacent convex portion 22b is adjusted (to be) within a predetermined range. Concretely, in a case of the third embodiment, since the divergence angle α is set to 20°, it is possible to realize by setting randomly the difference in the heights and the distance between the adjacent convex portions 22b in a range of approximately 50 μm or less. Here, when the difference in the height is too much or when the distance between the adjacent convex portions 22b is long, since it is not possible to achieve the stable divergence angle α, it is desirable to let both the difference in height and the distance between the two adjacent convex portions 22b to be about 100μ or less.

Figure 13:
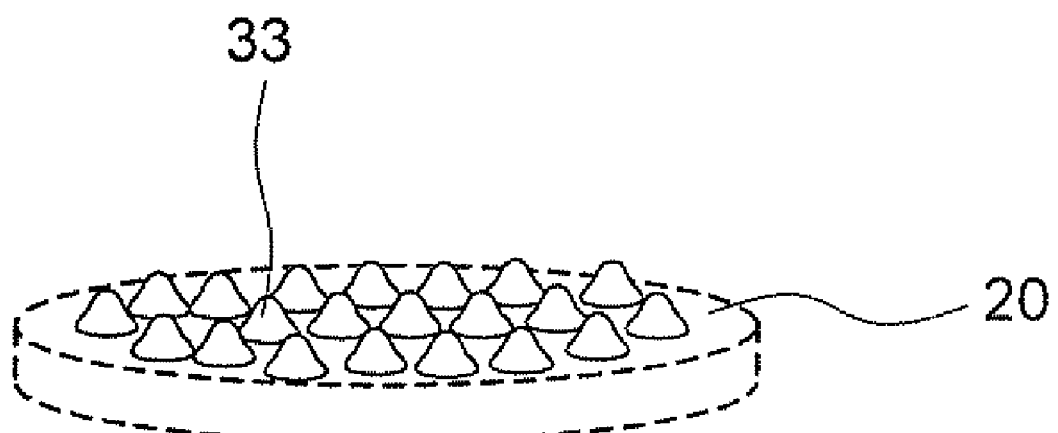
FIG. 13 is a diagram showing a modified example of the plate member.
Figure 14:
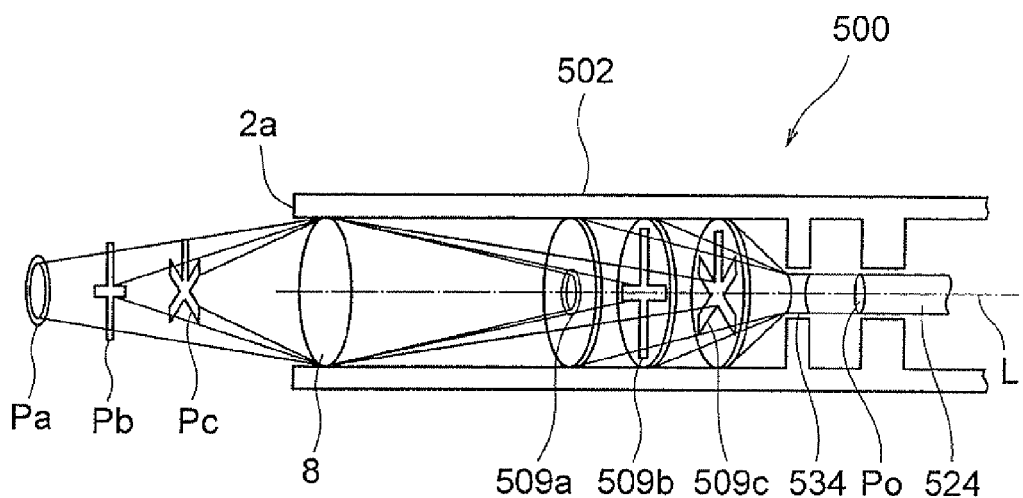
FIG. 14 is a diagram showing a cross-sectional view of main components of a conventional light source apparatus for endoscope.

In the third embodiment, a transparent substrate on which minute concavo-convex surface 22 is formed, is used as the plate member 20. However, it is not restricted to any particular member provided that it is an optical member having a divergence effect. As shown in FIG. 13, a plurality of minute convex lenses 33 may be formed on a surface of the plate member, or, a plurality of minute concave lenses may be formed on the surface of the plate member 20. FIG. 13 is a diagram showing a modified embodiment of the plate member 20.

An operation of the third embodiment will be described below while referring to diagrams from FIG. 9 to FIG. 12.

The excitation light emitted from the emitting end portion Po of the optical fiber 2 advances while spreading according to the NA of the optical fiber 2. Since the first taper angle θ of the side surface of the first cavity 9 (the first taper surface 9a) of the holding member 19 between the emitting end portion Po of the optical fiber 2 and the plate member 20 is greater than the angle of incidence φ which is calculated from the NA of the optical fiber 2, the excitation light, basically, without being irradiated to the first taper surface 9a, advances toward the plate member 20.

Here, due to bending and installing state of the optical fiber 2, sometimes, the excitation light is emitted at an angle greater than the angle of incidence φ calculated by from the NA of the optical fiber 2, from the emitting end portion Po of the optical fiber 2. A par of such light is irradiated to the side surface of the cavity 9 (the first taper surface 9a). Since the side surface of the cavity is a reflecting surface, such light is reflected at the side surface of the cavity, and a part of such light is irradiated toward the plate member 20. In this way, though the excitation light is irradiated directly on the first taper surface 9a, it is possible to reflect a part of it toward a direction of the plate member 20. As a result it is possible to let to be minimum, the loss of the excitation light due to the bending and installing state of the optical fiber.

As shown in FIG. 11, the concavo-convex surface 22 on the surface of the plate member 20 has a minute focal length, and accordingly, it is possible to diverge the excitation light on the wavelength converting member 4, over a wide range, than in the first embodiment and the second embodiment. It is possible to adjust a range of a height of a peak (a depth of a valley) of the convex portion 22b (concave portion 22a) of the concavo-convex surface 22 at the time of manufacturing, and to set such that the excitation light is irradiated exactly to the effective wavelength conversion area 14 on the wavelength converting member 4. Accordingly, for example, it is possible to set freely a divergence angle α in a range of a few degree to 40° or more.

As shown in FIG. 11, the excitation light irradiated from a lower side is incident on the concavo-convex surface 22 of the plate member 20 and refracted. Further, the excitation light advances in a diverging direction at the concave portion 22a, and advances in a diverging direction where the excitation light has crossed a focal length $P_3$ at the convex portion 22b.

A part of the excitation light is absorbed by the wavelength converting member 4, and becomes wavelength-converted light upon being subjected to wavelength conversion. A part of the wavelength-converted light is emitted as light irradiated from the reflecting side of the surface to which the excitation light of the wavelength converting member 4 is irradiated. Another part of the wavelength-converted light is irradiated to the inside of the second cavity 18 of the holding member 19 from the surface to which the excitation light has been irradiated. The wavelength-converted light upon being emitted to inside of the second cavity 18, by being reflected at the side surface of the side surface of the cavity 18 (the second taper surface 18a), the part of the wavelength-converted light upon passing through the wavelength converting member 4, is emitted from the emitting end portion.

As compared to the first embodiment, since the second taper angle ψ inside the second cavity 18 is formed to be large such that the excitation light is not irradiated directly, the excitation light which is emitted inside the second cavity 18 is reflected at the reflecting surface of the cavity side surface (the second taper surface 18a), and a part thereof is irradiated once again inside the cavity 18 in a side of emitting end portion $P_4$, in a state where an amount of light is much more than that of the first embodiment.

In the present embodiment, what differs substantially from the first embodiment and the second embodiment are optical characteristics of the plate member 20 which will be described below.

As mentioned above, the range of height of the peak (the depth of valley) of the convex portion 22b (the concave portion 22a) of the minute concavo-convex surface 22 is variable in a range of divergence angle α of the excitation light from a few degrees to near 50°. Therefore, by using the minute concavo-convex surface 22, it is possible to adjust a divergence effect.

Further, since the minute concave and convex portions on the concavo-convex surface 22 are formed at random in its size and its distance, the effect of diffusion is also random. Therefore, it is possible to diverge the excitation light uniformly to the effective wavelength conversion area 14 of the wavelength converting member 4. For example, though the excitation light having an intensity distribution such as a Gaussian beam, it is possible to reduce a difference in intensity distribution in Gaussian beam, and since it is possible to draw uniform light, it is possible to reduce unevenness in color.

Furthermore, since the plate member 20 has extremely high transmittance, it is possible to obtain bright emission of light with small loss of light intensity. Moreover, when the plate member 20 is let to be of a material in the form of a resin, it is possible to form a plate member in the form of a film. Furthermore, since the difference in the height of the concavo-convex surface, or the distance between adjacent concave portion, or the distance between the adjacent convex portion of the concavo-convex surface is of a size in a range of 10 microns to 100 microns, the focal length $P_3$ is of a size in a range of 10 microns to 100 microns. Therefore, it is possible to enlarge the diverging effect of the concave lens such as in the first embodiment and the second embodiment. Accordingly, it is possible to make the structure inside the holding member 19 to be small-sized.

Moreover, since it is not necessary to adjust the principal axis only by fixing the plate member 20 rather than disposing a lens as in the first embodiment and the second embodiment, it is possible to omit a process of axis adjustment.

In the third embodiment, an example in which, the entire excitation light is subjected to wavelength conversion to be fluorescent light has been cited. However, present invention is not restricted to such wavelength conversion. In other words, a part of the excitation light is subjected to wavelength conversion, and by allowing the remaining part of the excitation light to be transmitted through the wavelength converting member 4, it is possible to use mixed light of the excitation light and the fluorescent light as irradiation light. According to this arrangement, for example, by combining fluorescent light of yellow color, and excitation light of blue color it is possible to create pseudo white color. By selecting the divergence angle of the plate member 20 such that the angle of incidence of the fluorescent light and the angle of incidence of the excitation light are substantially same, it is possible to construct so that the mixed light of the excitation light and the fluorescent light irradiated from the emitting end is irradiated to substantially same area. As a result, it is possible to reduce unevenness in color of color mixture of the excitation light and the fluorescent light.

In the semiconductor light source apparatus according to the present invention, since a distance between a light diverging unit such as a concave lens and an emitting end portion Po of a optical fiber which guides the excitation light, and the wavelength converting member, and the light diverging means (unit) and a range of the effective area of the wavelength converting member are optimized, the semiconductor light source apparatus according to the present invention shows an effect that it is possible to improve an efficiency of the excitation light as well as to make small the overall apparatus.

What is claimed is:

1. A light source apparatus comprising:
a light source which emits excitation light;
an optical fiber which is optically connected to the light source, and which guides the excitation light;
a wavelength converting member which is optically connected to an emitting end portion of the optical fiber, and which receives the excitation light emitted from the emitting end portion, and makes emerge light of a wavelength area different from a wavelength area of the excitation light; and
a holding member which holds the emitting end portion of the optical fiber, a light diverging unit, and the wavelength converting member,
wherein the light source apparatus has the light diverging unit which is arranged in an optical path of the excitation light, between the emitting end portion of the optical fiber and the wavelength converting member, and
the holding member comprises:
a first internal space between the emitting end portion of the optical fiber and the light diverging unit, and
a second internal space between the light diverging unit and the wavelength converting member;
wherein the light diverging unit is a plurality of light diverging optical elements formed on a plate member, the plurality of light diverging optical elements formed on the plate member is a concavo-convex surface formed on a surface of the plate member and the concavo-convex surface is disposed at random such that a distance between the convex portion and an adjacent convex portion is not more than 100 microns.

2. The light source apparatus according to claim 1, wherein the light diverging unit has a function of widening a beam spot such that, a size of a beam spot formed on the wavelength converting member by the excitation light emitted from the optical fiber is substantially same as or smaller than a size of an effective wavelength conversion area of the wavelength converting member.

3. The light source apparatus according to claim 2, wherein the light diverging unit includes at least an optical member having a negative refracting power which guides light.

4. The light source apparatus according to claim 1, wherein a distance between a valley of a concave portion and a peak of a convex portion of the concavo-convex surface is not more than 100 microns.

5. The light source apparatus according to claim 1, wherein the light diverging optical element has a concavo-convex surface formed by an imprint method, on a surface of glass or resin.

6. The light source apparatus according to claim 1, wherein the light diverging element is a plurality of concave lenses formed on a surface of the plate member.

7. The light source apparatus according to claim 2, wherein a size of the light diverging unit is substantially same or larger as compared to the beam spot formed on the light diverging unit by the excitation light.

8. The light source apparatus according to claim 2, wherein a size of the wavelength converting member is substantially same or larger with respect to a beam spot formed on the wavelength converting member by the excitation light via the light diverging unit.

9. The light source apparatus according to claim 1, wherein:
the holding member has an area between the emitting end portion of the optical fiber and the wavelength converting member, on an inner surface of the holding member is a circular conical structure having a taper angle with respect to a principal axis of the excitation light, and having a side toward the wavelength converting member wider than a side toward the emitting end portion of the optical fiber.

10. The light source apparatus according to claim 9, wherein the circular conical structure on the inner surface of the holding member has a first taper angle $\theta$ defined as an angle between the principal axis of the excitation light and the inner surface of the holding member, between the emitting end portion of the optical fiber and the light diverting unit, and a second taper angle $\psi$ defined as angle between the principal axis of the excitation light and the inner surface of the holding member, between the light diverging unit and the wavelength converting member, mutually different.

11. The light source apparatus according to claim 10, wherein the second taper angle $\psi$ is greater with respect to the first taper angle $\theta$.

12. The light source apparatus according to claim 11, wherein when an angle of incidence $\phi$ of the excitation light emitted from the emitting end portion of the optical fiber is calculated as $\phi=\sin^{-1}$ NA by using a numerical aperture NA of the optical fiber, the first taper angle $\theta$ and the angle of incidence $\phi$ of the excitation light are related by a relation $\theta \geq \phi$.

13. The light source apparatus according to claim 9, wherein the inner surface of the holding member between the emitting end portion of the optical fiber and the wavelength converting member is a reflecting surface.

14. The light source apparatus according to claim 1, wherein the light diverging unit is one concave lens, and
the light source apparatus further comprises:
an optical unit which includes at least once convex lens between the light diverging unit and the wavelength converting member, which irradiates the excitation light spread by the light diverging unit, to the wavelength converting member, upon changing the excitation light to parallel light.

* * * * *